United States Patent
Won et al.

(10) Patent No.: US 10,279,047 B2
(45) Date of Patent: May 7, 2019

(54) COMPOSITIONS AND METHODS FOR MODIFYING THE SURFACE OF CELLS AND METHODS OF USE

(71) Applicant: UNIVERSITY OF UTAH RESEARCH FOUNDATION, Salt Lake City, UT (US)

(72) Inventors: Young-Wook Won, Salt Lake City, UT (US); David A. Bull, Salt Lake City, UT (US); Amit N. Patel, Salt Lake City, UT (US)

(73) Assignee: UNIVERSITY OF UTAH RESEARCH FOUNDATION, Salt Lake, UT (US)

( * ) Notice: Subject to any disclaimer, the term of this patent is extended or adjusted under 35 U.S.C. 154(b) by 76 days.

(21) Appl. No.: 15/113,009

(22) PCT Filed: Jan. 20, 2015

(86) PCT No.: PCT/US2015/012081
§ 371 (c)(1),
(2) Date: Jul. 20, 2016

(87) PCT Pub. No.: WO2015/109325
PCT Pub. Date: Jul. 23, 2015

(65) Prior Publication Data
US 2017/0000894 A1    Jan. 5, 2017

Related U.S. Application Data

(60) Provisional application No. 61/929,430, filed on Jan. 20, 2014.

(51) Int. Cl.
| | | |
|---|---|---|
| *A61K 47/00* | (2006.01) | |
| *A61K 38/00* | (2006.01) | |
| *A61K 47/44* | (2017.01) | |
| *A61K 47/50* | (2017.01) | |
| *A61K 47/48* | (2006.01) | |
| *C12N 5/00* | (2006.01) | |
| *C12N 5/0775* | (2010.01) | |
| *A61K 49/00* | (2006.01) | |
| *A61K 35/28* | (2015.01) | |
| *A61K 47/64* | (2017.01) | |
| *A61K 47/69* | (2017.01) | |
| *A61K 35/12* | (2015.01) | |

(52) U.S. Cl.
CPC ........ *A61K 47/48276* (2013.01); *A61K 35/28* (2013.01); *A61K 47/64* (2017.08); *A61K 47/6425* (2017.08); *A61K 47/6911* (2017.08); *A61K 49/0041* (2013.01); *A61K 49/0047* (2013.01); *A61K 49/0084* (2013.01); *C12N 5/0006* (2013.01); *C12N 5/0662* (2013.01); *C12N 5/0663* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 2008/0070830 A1 | 3/2008 | Dzau et al. | |
| 2009/0202621 A1* | 8/2009 | Maldonado | ............ A61K 9/127 424/450 |
| 2011/0165128 A1 | 7/2011 | Doronin et al. | |
| 2011/0171666 A1 | 7/2011 | Weinberg et al. | |
| 2012/0277158 A1 | 11/2012 | Castaigne et al. | |
| 2013/0202684 A1 | 8/2013 | Geall et al. | |

FOREIGN PATENT DOCUMENTS

| | | |
|---|---|---|
| CN | 101918841 A | 12/2010 |
| CN | 102781965 A | 11/2012 |
| CN | 103179984 A | 6/2013 |
| WO | 2009/134532 A2 | 11/2009 |
| WO | 2010/126319 | 11/2010 |

OTHER PUBLICATIONS

Kato et al. (2004, Biotechnol. Prog. 20:897-904).*
https://www.quantabiodesign.com/what-is-dpeg/, accessed May 4, 2018.*
International Search Report and Written Opinion for Application No. PCT/US2015/012081 dated Apr. 8, 2015 (10 pages).
Teramura et al. "Behavior of synthetic polymers immobilized on a cell membrane," Biomaterials 29 (2008) 1345-1355.
Teramura et al. "Cell surface modification with polymers for biomedical studies," The Royal Society of Chemistry, Soft Matter, 2010, 6, 1081-1091.
Won et al., "Cell surface engineering to enhance mesenchymal stem cell migration toward an SDF-1 gradient", Biomaterials, 2014, vol. 35, No. 21 , pp. 5627-5635.
Stephan et al., "Enhancing cell therapies from the outside in: Cell surface engineering using synthetic nanomaterials", NANO Today, 2011, vol. 6, No. 3, pp. 309-325.
Lee et al., "Antibody targeting of stem cells to infarcted myocardium", Stem Cells, 2007, vol. 25, No. 3, pp. 712-717.
Zhao W et al: "Chemistry and material science at the cell surface", Materials Today, 2010, vol. 13, No. 4, pp. 14-21.
Medof et al., "Cell-surface engineering with GPI-anchored proteins", The FASEB Journal, 1996, vol. 10, No. 5, pp. 57 4-586.

(Continued)

*Primary Examiner* — Elizabeth C. Kemmerer
(74) *Attorney, Agent, or Firm* — Michael Best & Friedrich LLP

(57) ABSTRACT

Described herein are compounds, compositions and methods for modification of the surface of a living cell with a therapeutically relevant targeting moiety. Also described herein are methods for treating disease states, such as acute myocardial ischemia or infarction, with said compositions, in a subject.

14 Claims, 15 Drawing Sheets

(56) References Cited

OTHER PUBLICATIONS

Lim et al., "Cell surface-engineering to embed targeting ligands or tracking agents on the cell membrane", Biochemical and Biophysical Research Communications, 2017, vol. 482, No. 4, pp. 1042-1047.
European Patent Office Extended Search Report for Application No. 15737194.9 dated Aug. 28, 2017 (15 pages).
Chinese Patent Office Action for Application No. 201580009487.2 dated May 30, 2018 (16 pages).
Frame et al., "Synthetic glycolipid modification of red blood cell membranes," Transfusion, 2007, 47(5):876-82.

* cited by examiner

COMPOSITIONS AND METHODS FOR MODIFYING THE SURFACE OF CELLS AND METHODS OF USE

CROSS-REFERENCE TO RELATED APPLICATIONS

This is a U.S. national stage entry of International Patent Application No. PCT/US2015/012081, filed on Jan. 20, 2015, which claims priority to U.S. Provisional Patent Application No. 61/929,430, filed on Jan. 20, 2014, the entire contents of all of which are fully incorporated herein by reference.

BACKGROUND

Cellular therapies, such as stem cell therapies, offer enormous hope for treating illnesses, diseases and tissue defects. A significant barrier for the effective implementation of cell therapies is the inability to target a large quantity of viable cells to tissues of interest with high efficiency. Systemic infusion is generally desired, because it minimizes the invasiveness of cell therapy and maximizes practical aspects of repeated doses. It also permits the cells to mimic natural cell trafficking processes and helps to ensure that cells remain in close proximity to oxygen and nutrient-rich blood vessels. However, cells generally exhibit poor homing capability or lose their capacity to home following ex vivo culture expansion.

For example, many pre-clinical studies suggest that mesenchymal stem cells (MSCs) have a beneficial effect on left ventricular (LV) remodeling and the recovery of cardiac performance following myocardial infarction (MI). As such, one would expect that it would be beneficial to treat MI by systemically infusing a patient with high concentrations of MSCs, such as autologous or allogeneic MSCs expanded in ex vivo culture. However, studies show that less than 1% of MSCs expanded in ex vivo culture typically reach the ischemic myocardium after systemic injection. This inefficiency in MSC homing is a consequence of various factors, but is primarily attributed to an absence of relevant cell surface homing ligands such as CXC chemokine receptor 4 (CXCR4). CXCR4 is a chemotactic receptor that recognizes the chemokine stromal-derived factor-1 (SDF-1), which is up-regulated in the ischemic myocardium after infarction and is believed to play a crucial role in cardiac recovery by recruiting CXCR4+ MSCs toward the SDF-1 gradient. Culture-expanded MSCs develop heterogeneous receptor expression and appear to lose key homing ligands, such as CXCR4, during cell culture, which contributes to the inefficiency of MSC homing in vivo. As most of the transplanted MSCs rapidly decline following IV infusion, there is a significant need to improve homing efficiency following systemic administration.

The culture expansion of MSCs for autologous administration takes several weeks to obtain the necessary number of MSCs needed for regenerative therapy, thus complicating the administration of MSC therapy in patients with an acute MI (AMI), who have a small therapeutic window. The cultivation of MSCs under hypoxia, treating MSCs with a cytokine cocktail, and virus-mediated CXCR4 transduction have all been shown to induce expression of CXCR4 on the surface of MSCs more quickly, but each of these approaches requires over 24 hours of MSC culture to induce CXCR4 expression. In turn, this may lead to significant changes in the properties of the MSCs. The key limitations in all of these approaches are the long-term processing time (>24 hours) to up-regulate CXCR4, the number of complicated steps, and the requirement for invasiveness to transfect DNA or to transduce a virus particle.

Because 1) the CXCR4/SDF-1 axis plays an important role in MSC homing to the ischemic myocardium, 2) SDF-1 is highly expressed up to 48 hours after infarction, and 3) the therapeutic window to treat patients with acute MI is small, the current approaches to induce CXCR4 expression, all of which require long-term MSC culture, are unlikely to be useful in a clinical setting. Therefore, a novel method to introduce CXCR4 on the surface of MSCs quickly (within an hour or less) is required for the allograft administration of MSCs to be a viable treatment for patients with an acute MI.

The surface modification of living cells with natural and synthetic polymers promises new opportunities in this arena. Recently, a variety of functional groups and bioactive substances have been introduced to the surface of various cell types. Methods employed in cell surface modification include covalent conjugation, hydrophobic interaction, and electrostatic interaction. Cell surface modifications, however, often cause severe cytotoxicity, or compromise the normal function of the cell. As such, it would be advantageous to develop new compositions and methods for quickly and efficiently modifying the surface of therapeutically important cell types, such as MSCs, with an appropriate targeting moiety without causing severe cytotoxicity and/or compromising the normal functioning of the cell.

SUMMARY

In one aspect, the disclosure provides a composition comprising the compound of formula (I):

$$L\text{-}Y\text{-}X\text{-}T \qquad (I).$$

L is a phospholipid.
Y is a poly(ethylene glycol).
X is a linker derived from a reactive functional group.
T is a targeting moiety adapted to bind to a target ligand.

In another aspect, the disclosure provides a method of localizing a cell to a location having associated therewith a target ligand, the method comprising delivering to the location a composition comprising the cell bound to the compound of formula (I):

$$L\text{-}Y\text{-}X\text{-}T \qquad (I).$$

L is a phospholipid.
Y is a poly(ethylene glycol).
X is a linker derived from a reactive functional group.
T is a targeting moiety adapted to bind to the target ligand.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
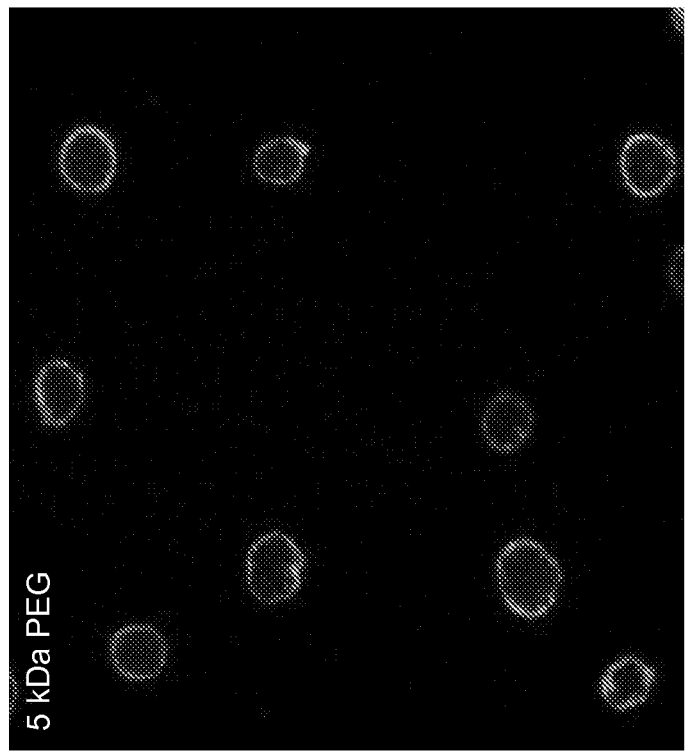
FIG. 1 is a series of confocal micrographs showing MSCs modified with DMPE-PEG-FITC compositions having different molecular weight PEG (3.4 and 5 kDa PEG).
Figure 1:
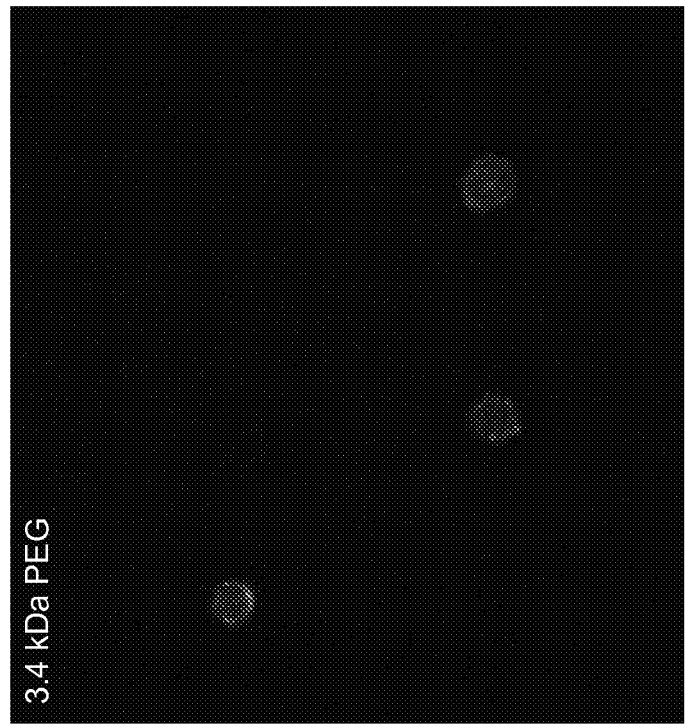

Described herein are pharmaceutical compositions and methods for modifying the surface of a living cell. Also described herein are methods of localizing a cell to a location having an associated target ligand, and for treating a subject suffering from myocardial ischemia or infarction.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

Section headings as used in this section and the entire disclosure herein are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" includes values slightly outside the cited values, namely, plus or minus 10%. Such values are thus encompassed by the scope of the claims reciting the terms "about" and "approximately." For example, the term "about" as used in connection with the size of poly(ethylene glycol) is intended to account for the fact that poly(ethylene glycol) is formed by a polymerization reaction, and generally has a distribution of sizes and molecular weights of approximately plus or minus 10%. Similarly, compositions formed using poly(ethylene glycol) also will have a distribution of sizes and molecular weights.

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Effective amount," as used herein, refers to a dosage of a compound or a composition effective for eliciting a desired effect. This term as used herein may also refer to an amount effective at bringing about a desired in vivo effect in an animal, mammal, or human, such as treating an acute MI.

As used herein, the term "subject" is intended to include human and non-human animals. An example of human subjects include a human patient having a disorder, e.g., an acute MI, or a normal subject. The term "non-human animals" includes all vertebrates, e.g. non-mammals (such as chickens, amphibians, reptiles), and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "chimeric antigen receptor" refers to an engineered receptor used to confer the specificity of an antibody onto a cell, such as a T cell.

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "phospholipid" refers to compounds that comprise a lipid moiety and a phosphate moiety. Commonly available phospholipids are those belonging to the glycerophospholipid class (also known as phosphoglycerols or as diacylglyceride phosphates), including, but not limited to 1,2-dimyristoyl-sn-glycero-3-phosphoethanolamine, 1,2-dipalmitoyl-sn-glycero-3-phosphoethanolamine and 1,2-distearoyl-sn-glycero-3-phosphocholine.

The term "targeting moiety" refers to any chemical entity that serves to target or direct the modified cell to a particular location or association (e.g., a specific binding event). Thus, for example, a targeting moiety may be used to direct a modified cell to a specific protein or enzyme, or to a particular cellular location, or to a particular cell type, in order to selectively enhance accumulation of the carrier cell.

Suitable targeting moieties include, but are not limited to proteins, peptides, glycoproteins, glycopeptides, steroids, polysaccharides, hormones, cofactors, nucleic acids, antibodies, chimeric antigen receptors, and drugs.

The term "target ligand" refers to the chemical entity which the targeting moiety is directed toward. For example, the target ligand may be a specific protein or enzyme in the body to which the targeting moiety becomes bound to or associated with, thereby increasing the accumulation of the modified cell carrying the targeting moiety in that particular physiological location.

The term "hydroxyl" refers to an —OH radical.

The term "amino" refers to a group of the formula —NHR, wherein R is selected from, for example, hydrogen, alkyl, alkenyl, alkynyl, cycloalkyl, heterocycle, aryl, arylalkyl, and heteroaryl. Examples of amino groups include but are not limited to —$NH_2$, alkylamino groups such as —$NHCH_3$, —$NHCH_2CH_3$ and —$NHCH(CH_3)_2$, and arylamino groups such as —NHPh. The group R may be optionally substituted with one or more substituents.

The term "carboxyl" refers to a —COOH radical.

The term "silane" refers to a group of the formula —$SiR^aR^bR^c$, wherein $R^a$, $R^b$, and $R^c$ are each independently selected from, for example, hydrogen, alkyl, alkenyl, alkynyl, cycloalkyl, heterocycle, aryl and heteroaryl.

The term "thiol" refers to an —SH radical.

The term "azide" refers to an —$N_3$ radical.

The term "substituents" refers to a group "substituted" on an alkyl, alkenyl, alkynyl, cycloalkyl, heterocycle, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein. For example, the abbreviations Me, Et and Ph represent methyl, ethyl and phenyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —$CH_2O$— optionally also recites —$OCH_2$—.

2. Compositions

Compounds that may be used in the methods and pharmaceutical compositions described herein include those having the following formula (I):

$$L-Y-X-T \quad (I)$$

wherein:

L is a phospholipid;

Y is a poly(ethylene glycol);

X is a linker derived from a reactive functional group; and

T is a targeting moiety adapted to bind to a target ligand.

L may be any suitable phospholipid capable of hydrophobically binding to the surface of a cell. L may include, but is not limited to: 1,2-dimyristoyl-sn-glycero-3-phosphoethanolamine (DMPE), 1,2-dipalmitoyl-sn-glycero-3-phosphoethanolamine, and 1,2-distearoyl-sn-glycero-3-phosphocholine. In some embodiments, L may be 1,2-dimyristoyl-sn-glycero-3-phosphoethanolamine (DMPE).

The poly(ethylene glycol) may have a molecular weight between about 2 kDa and about 10 kDa, such as about 3 kDa, about 3.4 kDa, about 4 kDa, about 5 kDa, about 6 kDa, about 7 kDa, about 8 kDa about 9 kDa, among others. In some embodiments, the poly(ethylene glycol) has a molecular weight of about 5 kDa.

The reactive functional group may include any functional group capable of reacting with another reactive group on a targeting moiety to form a covalent bond. As indicated above, this reaction forms linker X. Suitable reactive functional groups may include, but are not limited to a maleimide, a N-hydroxysuccinimide, a hydroxyl, an amino, a carboxyl, a thiol, a silane, and an azide, among others. In some embodiments, the reactive functional group may be maleimide.

The targeting moiety T may include any chemical entity capable of specifically binding a target ligand. Suitable targeting moieties may include, but are not limited to proteins, peptides, glycoproteins, glycopeptides, steroids, polysaccharides, hormones, cofactors, nucleic acids, antibodies, chimeric antigen receptors and drugs. Likewise, the target ligand may be any ligand capable of specific binding to the targeting moiety. Exemplary targeting moieties and target ligands are shown below in Tables 1-3. Tables 2 and 3 are reproduced from Nature Reviews Cancer, 2013, 13, 525-541. In these tables, the antigens listed may be an appropriate target ligand while the corresponding receptor may be the targeting moiety.

TABLE 1

Candidate signals for cell homing

| Targeting Moiety | Target tissue | Target | Target Ligand |
|---|---|---|---|
| PSGL-1/CD162 | Heart | Blood Vasculature | P-selectin |
| CRPPR | | | CRIP2; HLP; ESP-1 |
| CKRAVR | | | Sigirr; TIR8 |
| CPKTRRVPC | | | bc10 |
| CRSTRANPC | | | MpcII-3 |
| CARPAR | | | EST |
| Angiopep-2: TFFYGGSRGKRNNFKTEEY | Brain | Brain endothelial cells | LRP1 |
| CLSSRLDAC | | | |
| CLPVASC | Kidney | | |
| CD44 | ARF | ECM | HA |
| CXCR4 | | | SDF-1 |
| SWCEPGWCR | Pancreas | Capillaries and larger vessels | |

TABLE 2

Representative studies using ACT of gene-engineered T cells in mouse models of cancer

| Antigen | Receptor | Mouse model (first day of treatment) | Comments | Refs |
|---|---|---|---|---|
| CD19 | CAR:CD3ζ | B cell lymphoma in SCID·Beige mice (day 13) | 100% survival to day 77 | 176 |
|  |  | NALM·6 tumour in SCID·Beige mice (day 4) | 40% survival >100 days | 22 |
|  |  | A20 systemic disease (day 12) in immunocompetent mice | Long term survival of the majority of mice | 177 |
|  | CAR:CD28-CD3ζ | Systemic NALM·6 tumours in SCID·Beige mice (day 2) | 44% survival >200 days; 10% when treated with CAR-CD3ζ | 41 |
|  |  | 38c13 lymphoma either intraperitoneal (day 1) or subcutaneous (day 4) in C3H/HeN immunocompetent mice | Long-term survival beyond 100 days | 178 |
|  | CAR:CD137-CD3ζ | Human ALL in NOD-SCID γc+ mice (day 21) | 100% enhanced survival to >150 days | 179 |
| CD24 | CAR:CD28-fcRγ | Human pancreatic cancer in SCID mice. Established orthotopic tumours from CAPAC or WAPAC cells | Prolonged survival with eradication of some tumours | 180 |
| CEA | CAR:CD28-CD3ζ | Panc02-CEA pancreatic tumour cells. Established orthotopic tumours in CEA transgenic immunocompetent mice | Long-term tumour eradication in 67% of mice | 24 |
| ERBB2 | CAR: CD28-CD137-CD3ζ | BT-474 human breast cancer cells in SCID mice (day 10) | Suppression of tumour and enhanced survival of mice to >72 days | 42 |
| Influenza virus NP | TCR α and β chains | Subcutaneous EL4 lymphoma expressing NP (day 0) | Total tumour regression in all mice | 184 |
| Lewis Y | CAR:CD28-CD3ζ | OVCAR-3 ovarian tumour injected subcutaneously in NOD-SCID mice (day 7) | Suppression of tumour growth until day 47 | 28 |
| Mesothelin | CAR:CD28-CD137-CD3ζ | Mesothelioma injected subcutaneously in NOG mice (day 43) | Eradication of a proportion of tumours | 44 |
| SV40T | TCR α and β chains | Spontaneous prostate tumours expressing SV40 large T in mice | Suppression of tumour development | 185 |
| VEGRF2 | CAR:CD28-CD137-CD3ζ | Established subcutaneous tumour of various types (days 10-14) | Long term survival of 40-80% | 59 | aFR, a-folate receptor;
ACT, adoptive cell transfer;
ALL, acute lymphoblastic leukaemia;
CAR, chimeric antigen receptor;
CEA, carcinoembryonic antigen;
NOG, NOD-SCID-l12rg+;
NOD, nonobese diabetic;
SCID, severe combined immunodeficient;
TCR, T cell receptor;
VEGFR2, vascular endothelial growth factor receptor 2.

TABLE 3

Summary of published reports of genetically redirected T cells in clinical trials

| Target antigens | Cancers | Receptor | Year reported | Number of patients | Responses | Phase of trial and ID number | Refs |
|---|---|---|---|---|---|---|---|
| CD19 | Lymphoma and CLL | CAR: CD28-CD3ζ | 2012 | Seven | One CR, five PR and one SD | I/II: NCT00924326 | 113, 117 |
|  | CLL and B-ALL | CAR: CD28-CD3ζ | 2011 | Eight | Three SD to 6 months | I/II: NCT00466531 and NCT01044069 | 114 |
|  | NHL | CD28-CD3ζ and CD3ζ | 2011 | Six | Two SD to 10 months | I: NCT00586391 | 64 |
|  | CLL | CAR: CD137-CD3ζ | 2011 | Three | Two CR and 1 PR | I: NCT01029366 | 115 |
|  | ALL | CAR: CD137-CD3ζ | 2013 | Two | Two* | I: NCT01029366 | 120 |
|  | ALL | CAR: CD28-CD3ζ | 2013 | Five | Five | I: NCT01044069 | 186 |

TABLE 3-continued

Summary of published reports of genetically redirected T cells in clinical trials

| Target antigens | Cancers | Receptor | Year reported | Number of patients | Responses | Phase of trial and ID number | Refs |
|---|---|---|---|---|---|---|---|
| CD19 and CD20 | DLCL or NHL | CAR: CD3ζ and HSV-TK | 2010 | Four | None | I: BB-IND-8513 and BB-IND-11411 | 116 |
| CD20 | NHL | CAR: CD3ζ | 2008 | Seven | One PR, four SD and two NED maintained | I: NCT00012207 | 121 |
| | | CAR: CD137-CD28-CD3ζ | 2012 | Three | One PR and two NED maintained | I: NCT00621452 | 122 |
| CAIX | RCC | CAR: CD3ζ | 2011 | 11 | None | I: DDHK97-29 | 26, 187 |
| CD171 | Neuroblastoma | CAR: CD3ζ | 2007 | Six | One PR | I: BB-IND9149 | 110 |
| CEA | Colorectal and breast | CAR: CD3ζ | 2002 | Seven | Minor response in two patients | I: NCT00004178 | 109 |
| | Colorectal | TCR | 2011 | Three | One PR | I: NCT00923806 | 10 |
| ERBB2 | Colorectal | CAR: CD28-CD137-CD3ζ | 2010 | One | 0* | I/II: NCT-09-C-0041 | 127 |
| GD2 | Neuroblastoma | CAR: CD3ζ | 2011 | 19 | Three CR | I: NCT00085930 | 112 |
| aFR | Ovarian | CAR: FcRγ | 2006 | 12 | None | I: NCT00019136 | 27 |
| GP100 | Melanoma | TCR | 2009 | 16 | One CR and two PR | I: NCT00509496 | 106 |
| | | | 2010 | Ten | NI | I: NCT01176461 | 188 |
| Lewis Y | AML | CAR: CD28-CD3ζ | 2013 | Four | None | I: CTX08-0002 | 189 |
| MART1 | Melanoma | TCR | 2006 | 15 | One PR | I | 102 |
| | | | 2006 & 2009 | 31 | Four OR | II: NCT00706992 | 103, 104 |
| | | | 2009 | 20 | Six PR | II: NCT00509288 | 106 |
| MAGEA3 | Melanoma, oesophageal and synovial sarcoma | TCR | 2013 | Nine | One CR and 4 PR[1] | I/II: NCT01273181 | 125 |
| NYESO1 | Melanoma and sarcoma | TCR | 2011 | 17 | Two CR and seven PR | II: NCT00670748 | 107 |
| | Multiple myeloma | TCR | 2012 | 11 | Three CR and seven PR | II: NCT01352286 | 190 |
| p53 | Melanoma | TCR | 2010 | 14 | NI | II: NCT00393029 | 37 |
| PSMA | Prostate | CAR: CD3ζ | 2013 | Five | Two PR | I: NCT100664196 | Personal communication[2] |
| TAG72 | Colorectol | CAR: CD3ζ | 1998 | 16 | One SD | I | 108 | aFR, a-folate receptor; ALL, acute lymphoblastic leukaemia; AML, acute myeloid leukaemia; B-ALL, B cell acute lymphocytic leukaemia; CAIX, carbonic anhydrase IX; CAR, chimeric antigen receptor; CEA, carcinoembryonic antigen; CLL, chronic lymphocytic leukaemia; CR complete response; DLCL, diffuse large cell lymphoma; MAGE, melonoma antigen; MART1, melanoma antigen recognized by T cells; NED, no evidence of disease; NHL, non-Hodgkin's lymphoma; NI, no information; OR objective response; PR, partial response; PSMA, prostate specific membrane antigen; RCC, renal cell carcinoma; SD, stable disease; TAG72, tumour-associated glycoprotein 72; TCR, T cell receptor.
*Patient relapsed with antigen-negative disease.
[1]Patient death on Study;
[2]R. P. Junghans, O. Z. Ma, R. Rathore, E. M. Gomes, A. J. Bais, A. S Y. Lo, M. Abedi, R. A. Davies, H. I. Cabral, A. S. Al-Homsi and S. I. Cohen personal communication.

In some embodiments, the targeting moiety may be CXCR4 and the target ligand may be SDF-1. In some embodiments, the targeting moiety may be Cys-Arg-Pro-Pro-Arg (CRPPR) and the target ligand may be CRIP2.

In some embodiments, L may be 1,2-dimyristoyl-sn-glycero-3-phosphoethanolamine (DMPE), the reactive functional group may be maleimide and the targeting moiety T may be CXCR4. In some embodiments, the poly(ethylene glycol) further may have a molecular weight of about 5 kDa.

In some embodiments, the compound of formula (I) may be bound to the surface of a cell, where L interacts hydrophobically with the lipid bilayer wall of the cell. Any suitable cell type may be surface-modified by the compound of formula (I), including, but not limited to, a white blood cell, an endothelial cell, a hepatocyte, a kuppfer cell, a hepatic stellate cell, an allogeneic stem cell, an autologous stem cell, an NK cell, a T cell, an endothelial progenitor cell, an hematopoietic stem cell, a pluripotent stem cell, an induced pluripotent stem cell, a lymphokine activated killer cell, and a dendritic cell. In some embodiments, the cell bound to the compound of formula (I) may be a mesenchymal stem cell.

Suitable compounds of formula (I) may include the following:

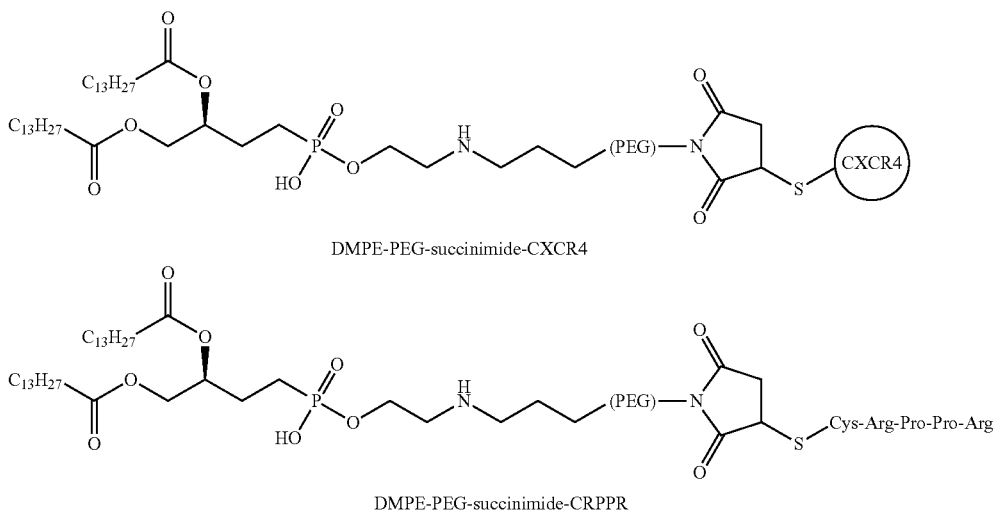

DMPE-PEG-succinimide-CXCR4

DMPE-PEG-succinimide-CRPPR

Other compounds include those compounds described herein.

a. Preparation of Compounds

Certain compounds described herein may be commercially available. Others may need synthetic preparation. For the preparation of compounds of Formula I, a phospholipid-PEG intermediate carrying a reactive functional group on the terminus of the PEG, may be coupled with a targeting moiety.

For example, when the reactive functional group is NHS, the intermediate may couple with a targeting moiety that has a reactive amino group to form an amide. When the reactive functional group is an amine, the intermediate may couple with a reactive isothiocyanate to form a thiocarbamate. When the reactive functional group is an azide, the intermediate may couple with targeting moieties that have a reactive nitrile or a reactive alkyne group to form a tetrazole or a triazole. When the reactive functional group is maleimide, the intermediate may couple with a targeting moiety that has a reactive thiol group to form a bond between the sulfur of the thiol and carbon of the resulting succinimide.

As a further example, and as illustrated in Scheme 1, commercially available DMPE-PEG-maleimide 1, can be coupled to recombinant CXCR4 through one of its 8 cysteine side chain residues to provide compound 3. Specific experimental details are described in the Examples.

Scheme 1. Synthesis of Compound 3

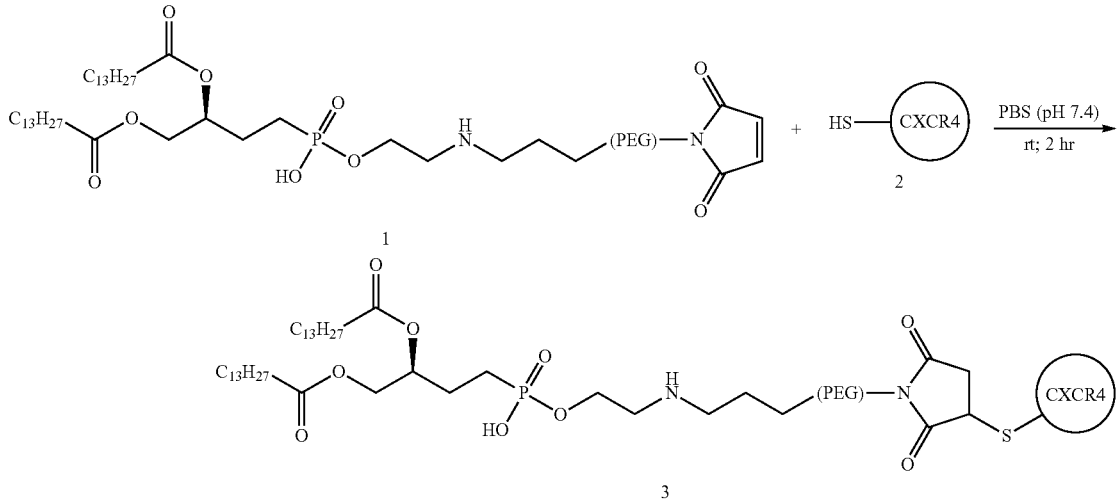

Other compounds described herein may also be prepared according to the methods set forth in Scheme 1.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and de-protection) useful in synthesizing the compounds described herein are known in the art and include, for example, those such as described in R. Larock, Comprehensive Organic Transformations, VCH Publishers (1989); T. W. Greene and P.G.M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

b. Surface Modification of Cells

As discussed above, the compounds of Formula (I) may be used to modify the surface of a cell, such as an MSC. Surface modification of a cell can be achieved by the phospholipid portion of the compound interacting with, and binding to the lipid bilayer membrane of the cell.

Each component, or variable, of the compound of Formula I may be evaluated to determine preferred compounds and their ability to modify the surface of a cell. Compounds possessing differing molecular weights of PEG may be utilized to determine which PEG size is preferable for the interaction between the phospholipid and cell membrane. The choice of reactive functional group attached to the terminus of the PEG may also be evaluated, depending on the targeting moiety being attached and the compatibility of the reactive functional groups it possesses. In addition, the minimum incubation time with the cell, along with the optimized quantity of the compound required for cell modification may also be determined.

Experiments that may determine certain abilities of the modified cells may be conducted. These may include experiments focused on cell adhesion, toxicity, proliferation, and recovery rate. In addition, kinetic experiments may determine the length of time which the compound can remain immobilized on the surface of the cell.

Additionally, the use of different targeting moieties may be evaluated to determine their effect on the ability of the compound of Formula I to modify the cell. Different fluorescent chemical entities, such as fluorescein isothiocyanate (FITC) and green fluorescent protein (GFP), may also be attached to or replace the targeting moiety for evaluation of the compound's ability to modify the cell.

Binding of the Target Ligand to the Targeting Moiety on the Surface of Cells

Evaluation of the binding of a target ligand to a targeting moiety on the surface of a cell may be achieved by incubating a fluorescent-labeled target ligand with a cell modified by a compound of Formula I that contains a fluorescent-labeled targeting moiety.

Modified Cell Migration Toward a Target Ligand

Migration of cells modified with the compound of Formula I toward the gradient of an appropriate target ligand may be achieved by incubation of the modified cell with the target ligand. Evaluation of the modified cell's ability to migrate may be determined by appropriate cell counting assays.

Further description of methods used to evaluate compounds can be found in the Examples.

4. Methods of Use

The methods described herein include methods of treating disease states in a subject in need of treatment, comprising administering to the subject a therapeutically effective amount of a composition described herein. The composition for administration to the subject in need may be comprised of a compound, such as a compound of formula (I) that is comprised of a targeting moiety, and a living cell bound to the compound of formula (I), wherein the compound interacts hydrophobically with the lipid bilayer wall of the cell. Also described herein are methods of promoting in vivo homing of the described composition to a target ligand, wherein the targeting moiety may bind or interact with a target ligand that is associated with a particular diseased tissue, and the modified cell may be recruited to the diseased tissue.

For example, the methods described herein include methods of treating acute myocardial infarction in a subject in need of treatment, comprised of administering to the subject a therapeutically effective amount of a composition described herein. The composition for administration to the subject in need is comprised of a compound, such as a compound of formula (I) that is comprised of the targeting moiety CXCR4, and an MSC bound to the compound of formula (I), wherein the compound interacts with the lipid bilayer wall of the cell. Also described herein are methods of promoting in vivo homing of the described CXCR4 modified MSC to the target ligand SDF-1, wherein CXCR4 binds SDF-1, and the modified MSC is recruited to the ischemic myocardium.

These methods may include the use of the compound of formula (I) for modification of cells such as endothelial cells, hepatocytes, kuppfer cells, and hepatic stellate cells for the treatment of liver diseases.

These methods may include the use of the compound of formula (I) for modification of cells such as T cells, NK cells, dendritic cells, and lymphokine activated killer cells for the treatment of cancer. For example, rather than using a retrovirus (such as a lentivirus) to modify a T-cell to include a chimeric antigen receptor, the T cell may be modified using the compound of formula (I), where the targeting moiety comprises the chimeric antigen receptor.

These methods may include the use of the compound of formula (I) for modification of cells such as allogenieic stem cells, autologous stem cells, endothelial progenitor cells, hematopoietic stem cells, pluripotent stem cells, and induced pluripotent stem cells for the treatment of cardiovascular disease.

These methods may include the use of the compound of formula (I) for modification of cells such as pluripotent stem cells and induced pluripotent stem cells for the treatment of eye disease, bone disease, neurodegenerative disorders, and other degenerative diseases.

These methods may include the use of the compound of formula (I) for modification of cells such as white blood cells, hematopoietic stem cells, pluripotent stem cells, and induced pluripotent stem cells for the treatment of blood disorders.

These methods may include the use of the compound of formula (I) for modification of cells such as T cells, NK cells, white blood cells, and dendritic cells for the treatment of immune disorders.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to: the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

The present disclosure has multiple aspects, some of which are illustrated by the following non-limiting examples.

Example 1

Synthesis of Compounds

General Experimental and Analytical Details

Functionalized DMPE-PEGs (3.4 kDa and 5 kDa) were purchased from Nanocs, Inc. (New York, N.Y.). Fluorescein isothiocyanate (FITC) and rhodamine were purchased from Thermo Scientific (Rockford, Ill.).

$^1$H and $^{13}$C NMR spectra were recorded on a Bruker AM 400 spectrometer (operating at 400 and 101 MHz respectively) or a Bruker AVIII spectrometer (operating at 500 and 126 MHz respectively) in CDCl$_3$ with 0.03% TMS as an internal standard or DMSO-d$_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 um column; UV detection wavelength=214 nm; flow rate=0.4 ml/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis(1H, 1H, 3H-tetrafluoropropoxy) phosphazine; and a make-up solvent of 90:10:0.1 MeOH:Water:Formic Acid which was introduced to the LC flow prior to the source to assist ionization.

DMPE-PEG-FITC

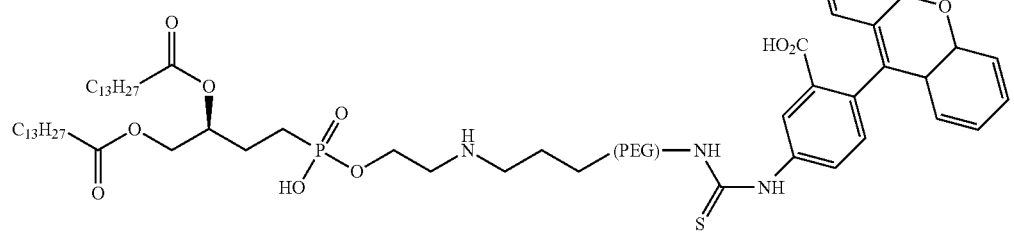

DMPE-PEG-NH$_2$ was dissolved at a concentration of 2 mg/ml in conjugation buffer (50 mM borate buffer, pH 8.5). FITC was dissolved in DMSO at 10 mg/ml and then 15-fold molar excess of FITC was added to the DMPE-PEG-NH$_2$ solution. The mixture was incubated under gentle shaking for 1 hour at room temperature in the dark. Excess and hydrolyzed FITC was removed with a Dye Removal Column (Thermo Scientific, Rockford, Ill.). DMPE-PEG-FITC was used immediately.

DMPE-PEG-GFP

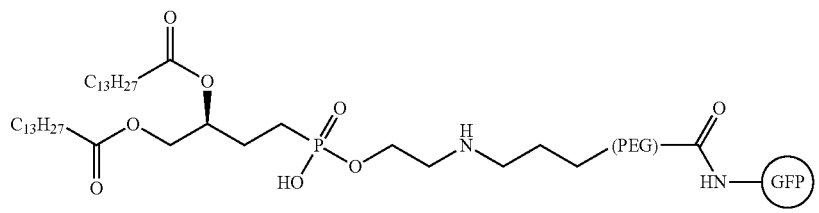

DMPE-PEG-NHS was dissolved in PBS (pH 7.4) at a concentration of 1 mg/ml. Stock solutions of GFP were prepared according to the manufacturer's instruction. Excess amount of DMPE-PEG (10- to 20-fold molar excess) was added to the GFP stock solution and incubated for 2 hours at room temperature. Impurities were removed by using Amicon Ultra Centrifugal Filters (Ultracel—10 kDa; Millipore, Billerica, Mass.). DMPE-PEG-GFP was kept at −80° C. until use.

DMPE-PEG-CXCR4

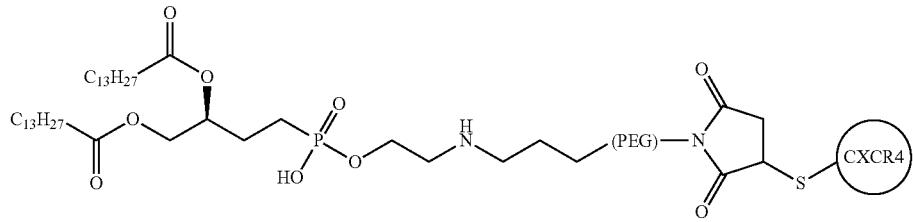

DMPE-PEG-maleimide was dissolved in PBS (pH 7.4) at a concentration of 1 mg/ml. A stock solution of rCXCR4 (50 ug/ml) was prepared according to the manufacturer's instruction. Excess DMPE-PEG-maleimide (10- to 20-fold molar excess) was added to the rCXCR4 stock solution and incubated for 2 hours at room temperature. Impurities were removed by using Amicon Ultra Centrifugal Filters (Ultracel—10 kDa; Millipore, Billerica, Mass.). DMPE-PEG-CXCR4 was kept at −80° C. until use.

DMPE-PEG-CRPPR

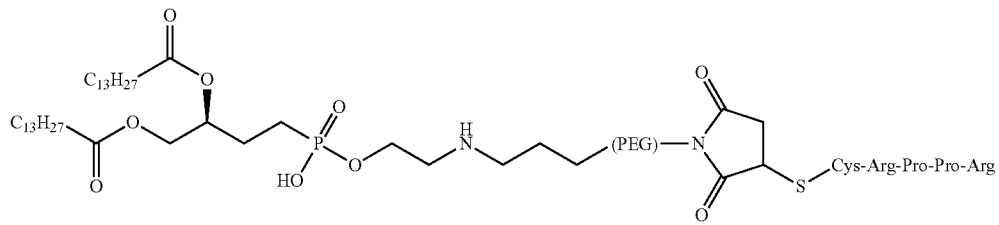

DMPE-PEG-CRPPR was prepared using the same method as employed for the preparation of DMPE-PEG-CXCR4.

Example 2

MSC Modification

General Experimental Procedures:

Culture expanded MSCs were harvested and suspended in phenol red-free media. DMPE-PEG or DMPE-PEG-CXCR4 was added directly to the cell suspension. At the predetermined time points, MSCs were harvested, washed, and suspended in HBSS. To optimize the amount of DMPE-PEG, different amounts of DMPE-PEG were mixed with 750,000 MSCs.

Effect of PEG Size on MSC Surface Modification:

Two DMPE-PEG compositions having differing PEG size, 5 kDa and 3.4 kDa, were labeled with FITC for fluorescence detection, and the DMPE-PEG-FITC compounds were subsequently incubated with MSCs in suspension. The compounds' abilities to bind to the surface of the MSC were evaluated by confocal micrograph and FACS analysis (see FIG. 1). Results demonstrated that incorporation of 5 kDa PEG into the composition was superior to use of 3.4 kDa PEG. All subsequent experiments described herein utilized DMPE-PEG compositions with 5 kDa PEG.

Figure 2:
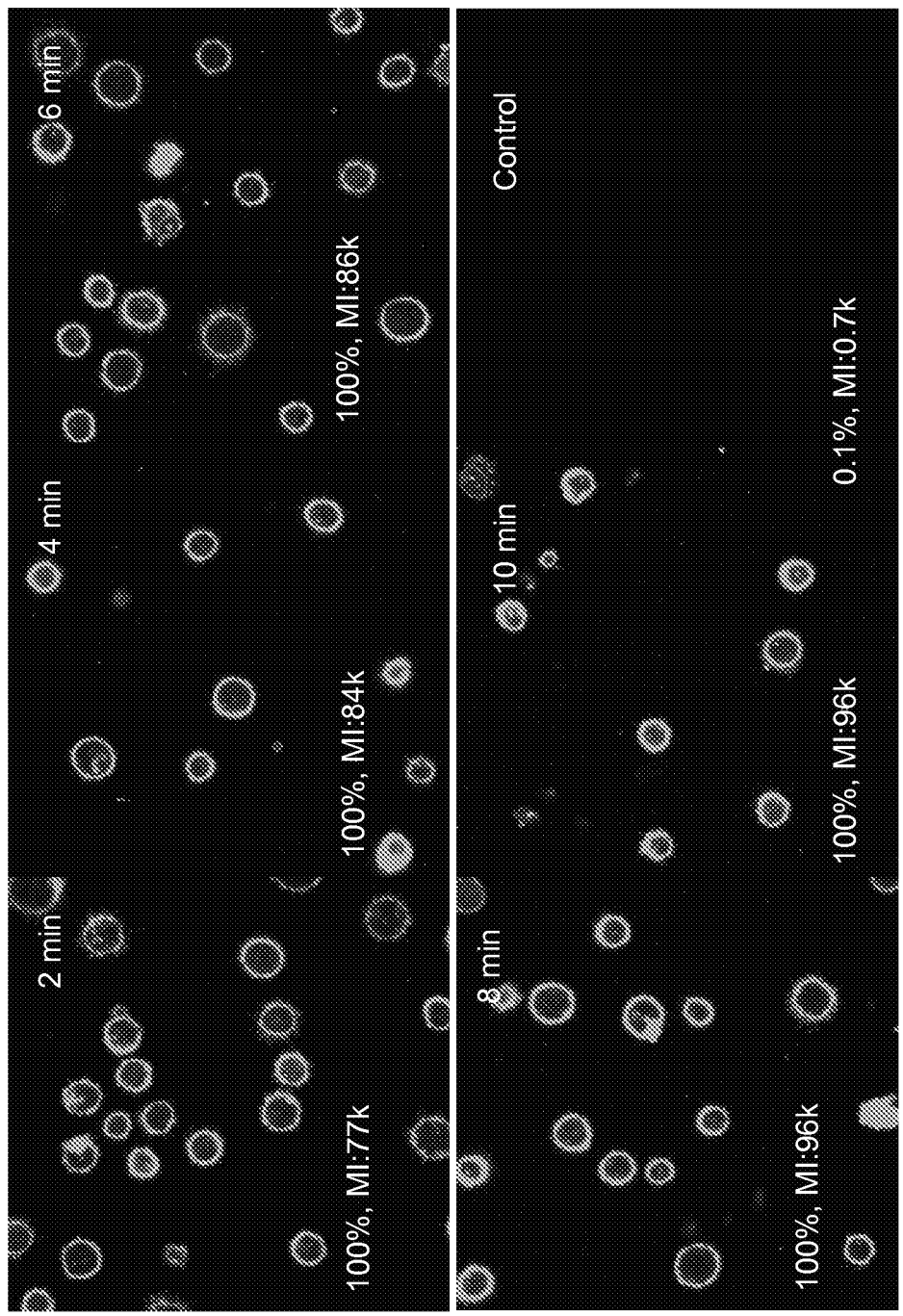
FIG. 2 is a series of confocal micrographs demonstrating the effect of incubation time of DMPE-PEG-FITC with MSCs on the modification yield.

Optimization of Incubation Time of DMPE-PEG:

MSCs were incubated with DMPE-PEG (5 kDa)-FITC for 10 minutes. During the incubation, MSC samples were taken at 2-minute intervals for confocal and FACS analysis. No measurable difference in the modification yield was observed as 100% of the total MSCs were modified at each time point (see FIG. 2).

Figure 3:
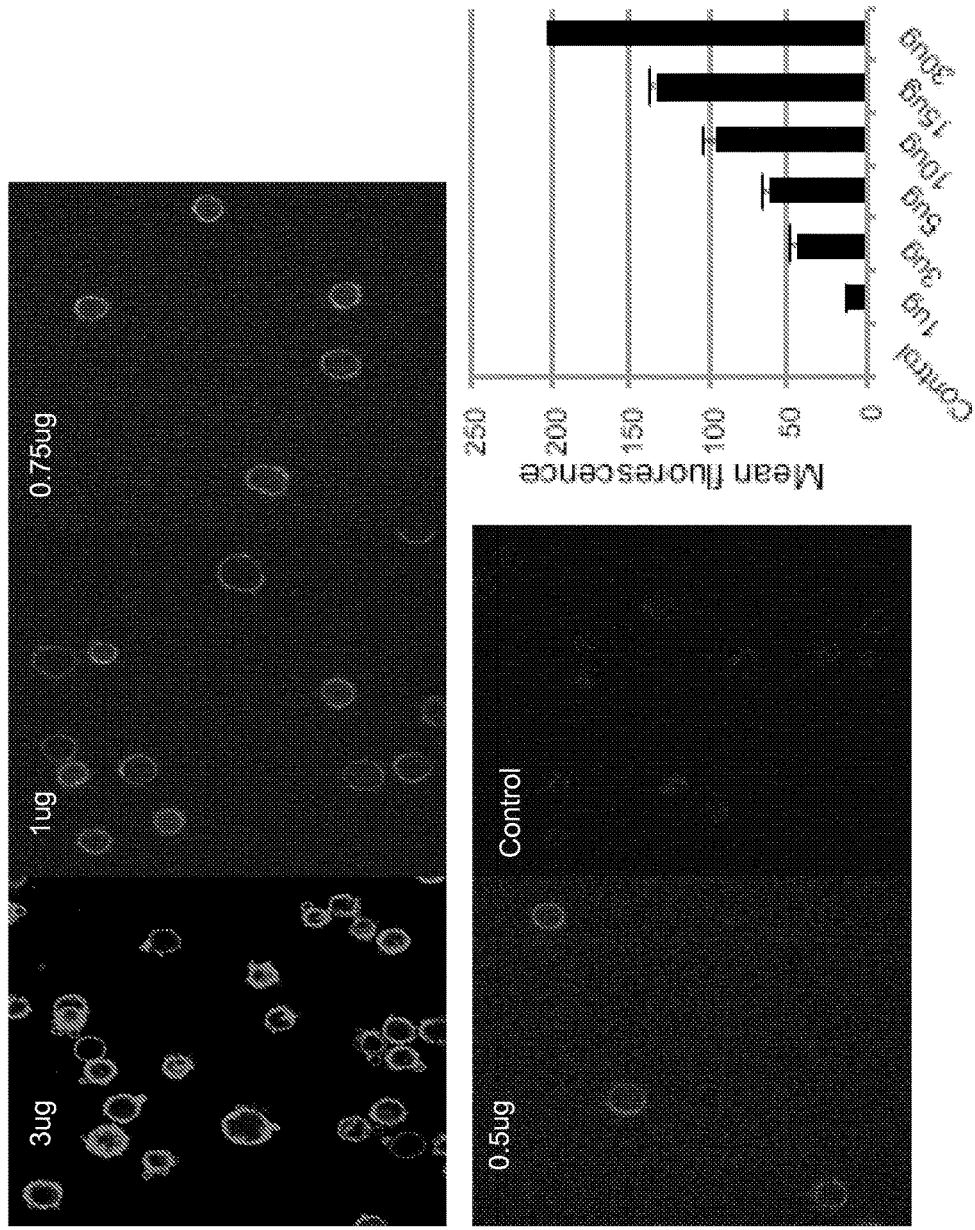
FIG. 3 is a series of confocal micrographs and a graph demonstrating the effect of the DMPE-PEG-FITC (ug/750,000 MSCs) on the modification yield of MSCs.

Optimization of the Amount of DMPE-PEG:

Varying amounts of DMPE-PEG (5 kDa)-FITC (1 ug, 3 ug, 5 ug, 10 ug, 15 ug, 30 ug) were combined with a fixed number of MSCs (750,000) for two minutes. All DMPE-PEG-FITC amounts effectively modified 750,000 MSCs. The amount of DMPE-PEG-FITC incorporated was measured as micrograms of the DMPE-PEG-FITC per 750,000 MSCs. Fluorescence intensity gradually increased in a dose-dependent manner (see FIG. 3).

Figure 4:
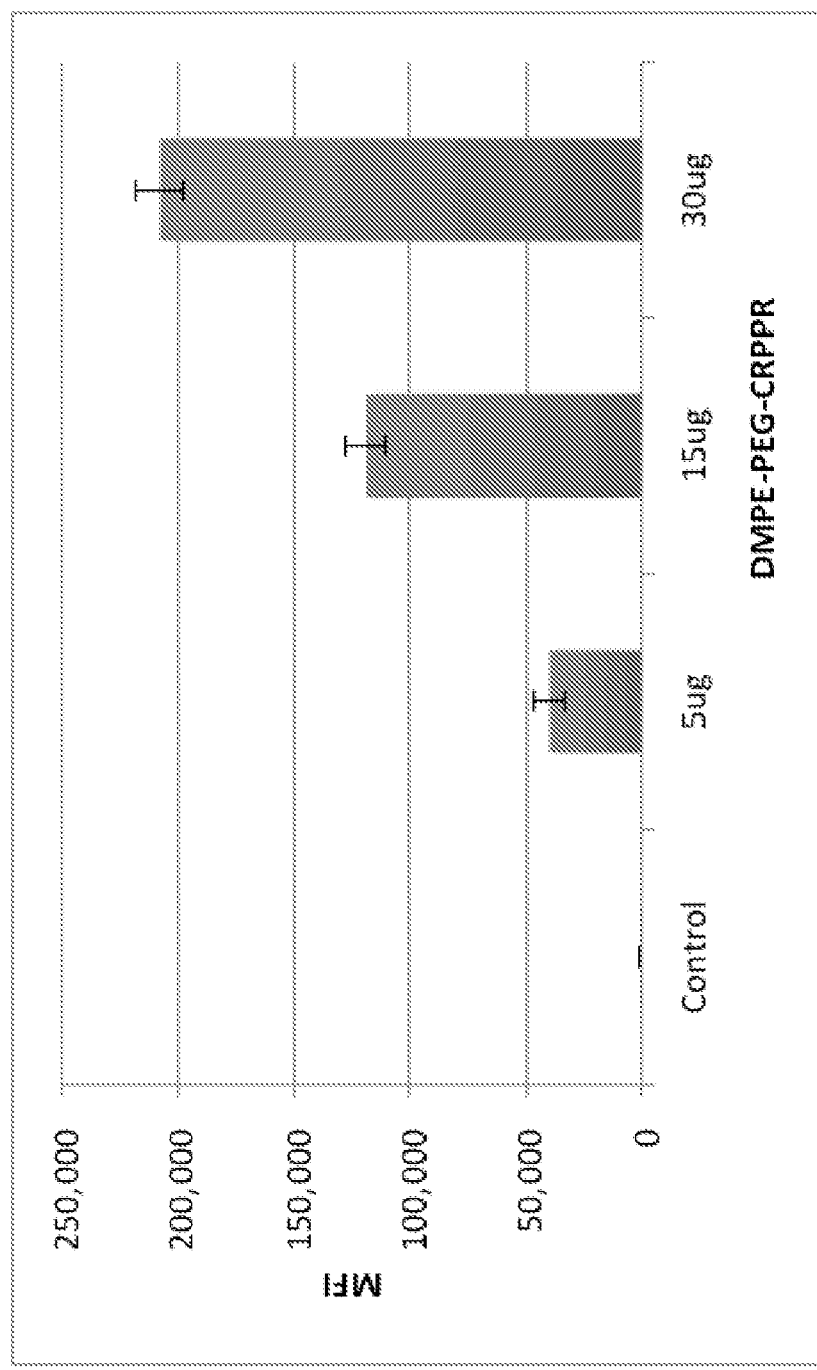
FIG. 4 is a graph demonstrating the effect of the DMPE-PEG-CRRPR amount on the modification yield of MSCs.

Using the Same Methods as Described Above for DMPE-PEG-FITC, varying amounts of DMPE-PEG (5 kDa)-CRPPR-FITC (5 ug, 15, ug, 30 ug) were incubated with MSCs for 10 minutes. A dose response was observed, with the most efficient modification observed for addition of 30 ug of the DMPE-PEG (5 kDa)-CRPPR-FITC conjugate (FIG. 4).

Figure 5:
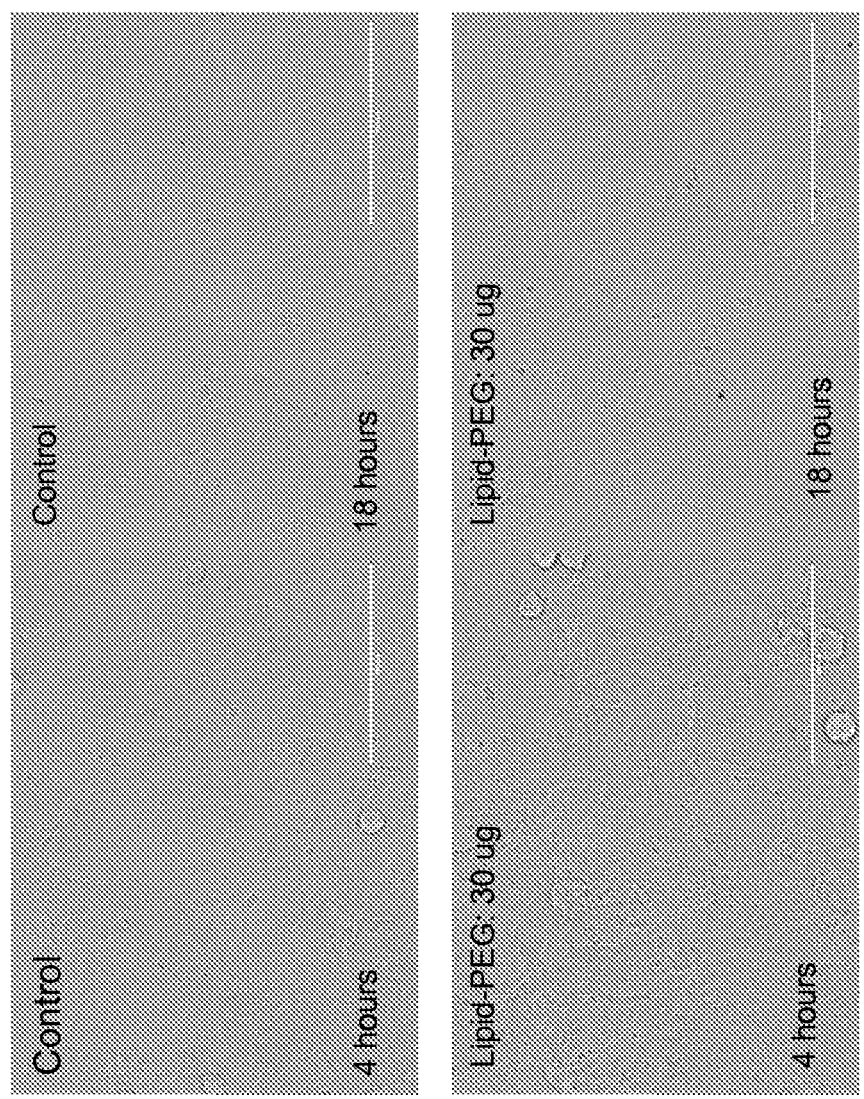
FIG. 5 is a series of micrographs demonstrating the cell attachment abilities of DMPE-PEG-FITC modified MSCs and non-modified MSCs.

Cell Adhesion:

MSCs were incubated with DMPE-PEG (5 kDa)-FITC (30 μg/750,000 MSCs) for 10 minutes, washed, and seeded on a well plate. After 4 and 18 hours, cell adhesion was observed by microscopy. Microscopy at 4 hours and 18 hours post-seeding showed no significant difference between the control (non-modified MSC) and the DMPE-PEG-FITC modified MSC with regards to cell adhesion (FIG. 5), suggesting that cell modification with DMPE-PEG (5 kDa)-FITC has no influence on other adhesive molecules located on the surface of MSCs and MSCs modified by this technique will not show any defects in attachment to the host tissue upon homing to the ischemic myocardium.

Figure 6:
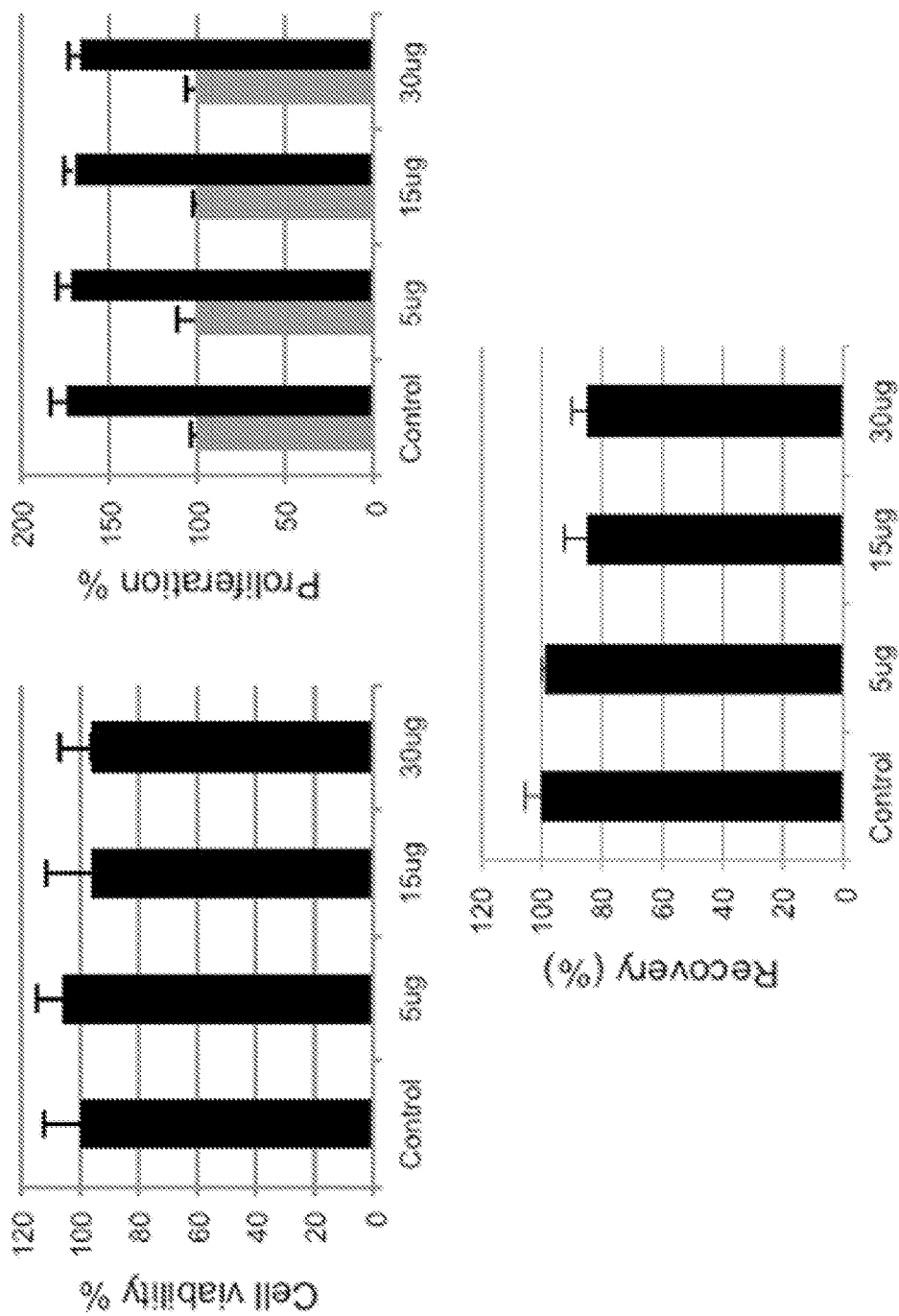
FIG. 6 is a series of graphs illustrating the cytotoxicity of DMPE-PEG-FITC, proliferation of DMPE-PEG-FITC modified MSCs, and recovery rate of DMPE-PEG-FITC modified MSCs.

Toxicity, Proliferation, and Recovery:

MSC viability after modification with DMPE-PEG (5 kDa)-FITC was determined by MTT assay and proliferation was determined using a cell proliferation kit (Molecular Probes; Eugene, Oreg.). Harvested MSCs after the modification were stained with trypan blue and counted to calculate the recovery rate. The DMPE-PEG-FITC composition was non-toxic to MSCs and the modified MSCs were capable of proliferating at the same rate as control cells (non-modified MSCs). In addition, recovery rates of the DMPE-PEG-FITC modified MSC were high (see FIG. 6).

Figure 7:
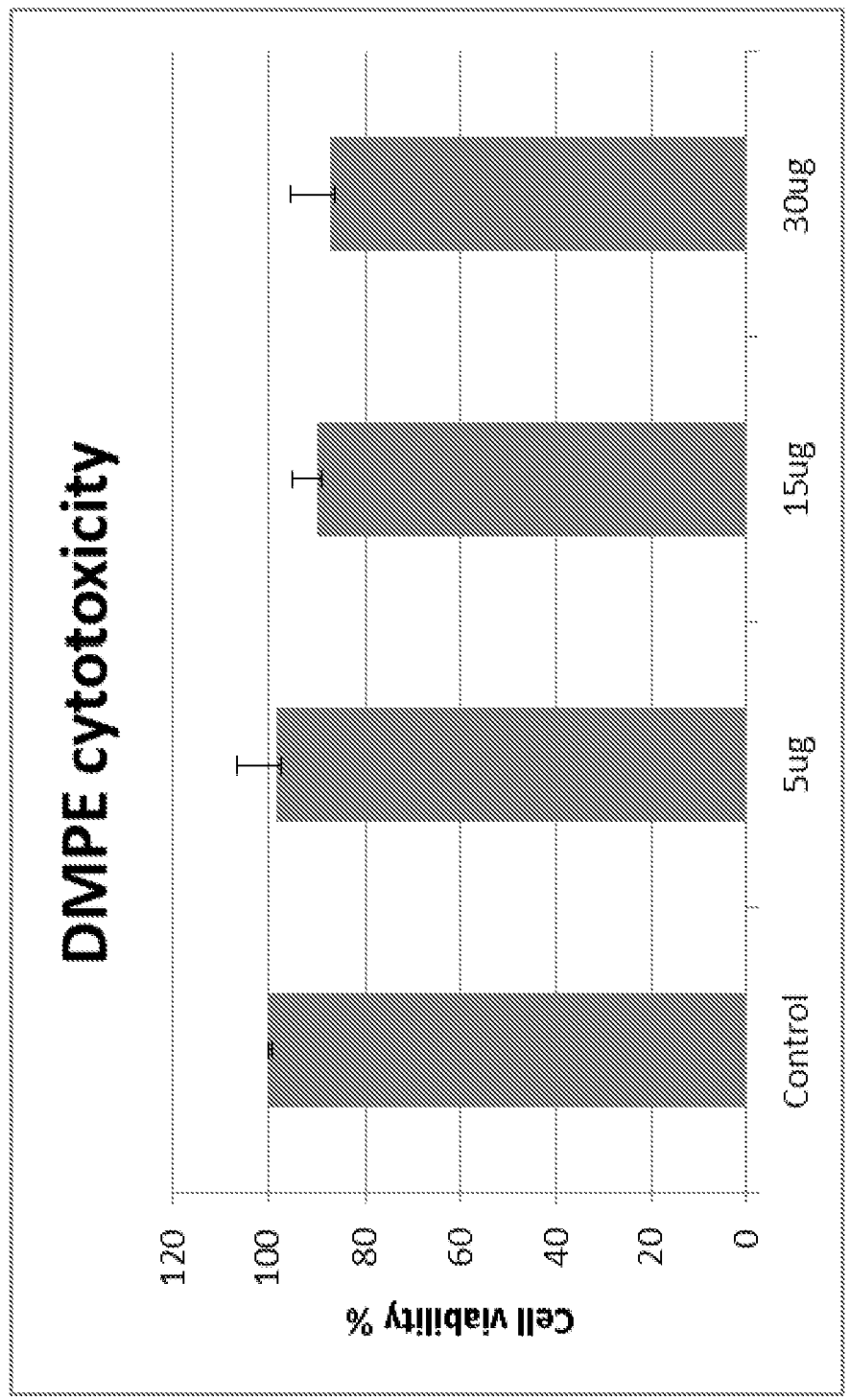
FIG. 7 is a graph illustrating the cytotoxicity of DMPE-PEG-CRPPR modified MSCs.
Figure 8:
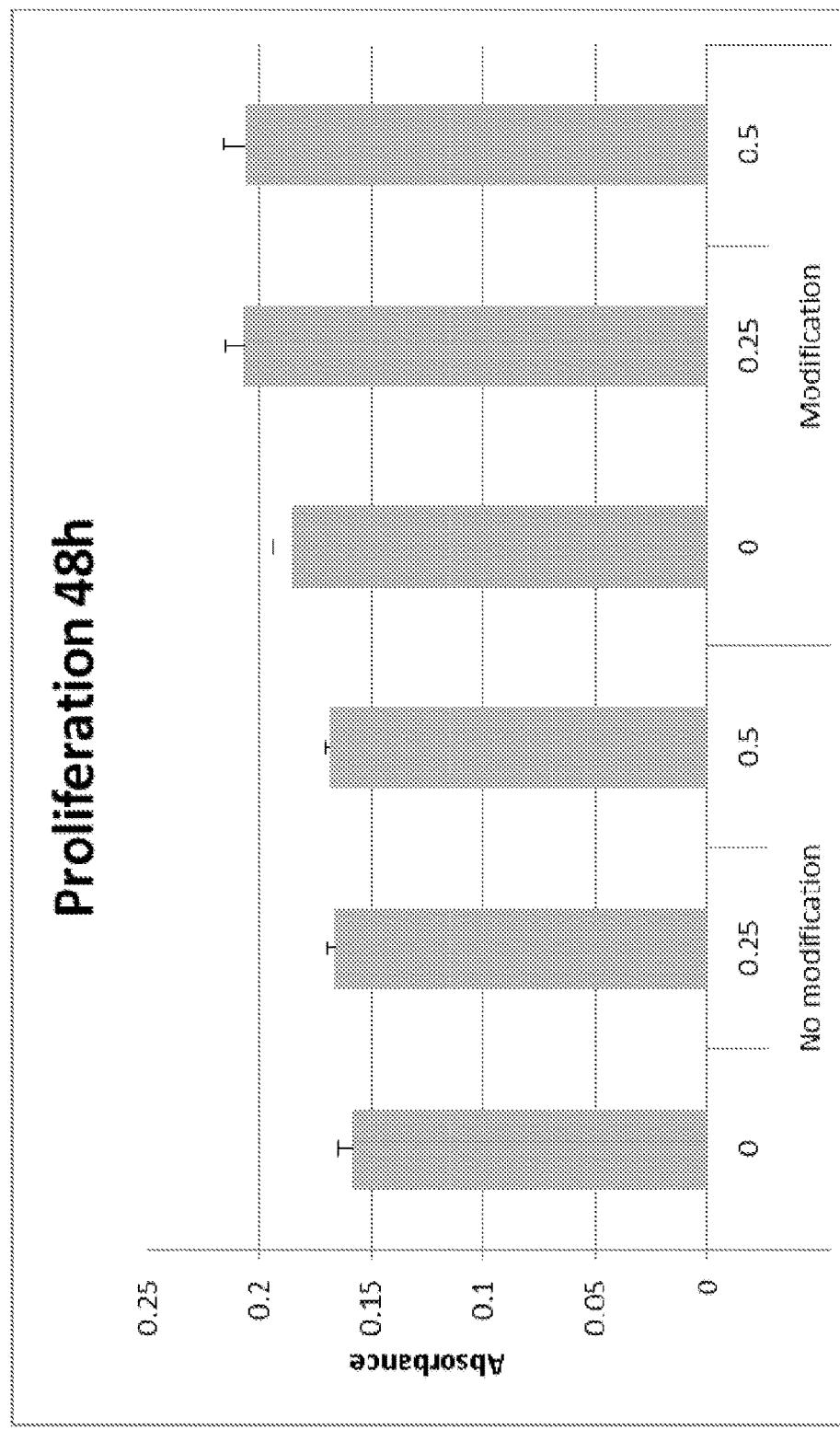
FIG. 8 is a graph illustrating the proliferation of DMPE-PEG-CRPPR modified MSCs.

Using the Same Methods as Described Above for DMPE-PEG-FITC Modified MSCs, the cytotoxicity and proliferation of DMPE-PEG (5 kDa)-CRPPR were also determined (see FIG. 7 and FIG. 8).

These results suggest that DMPE-PEG modified MSCs may have no side effects in the body after administration and the modified MSCs may proliferate normally upon engraftment.

Figure 9:
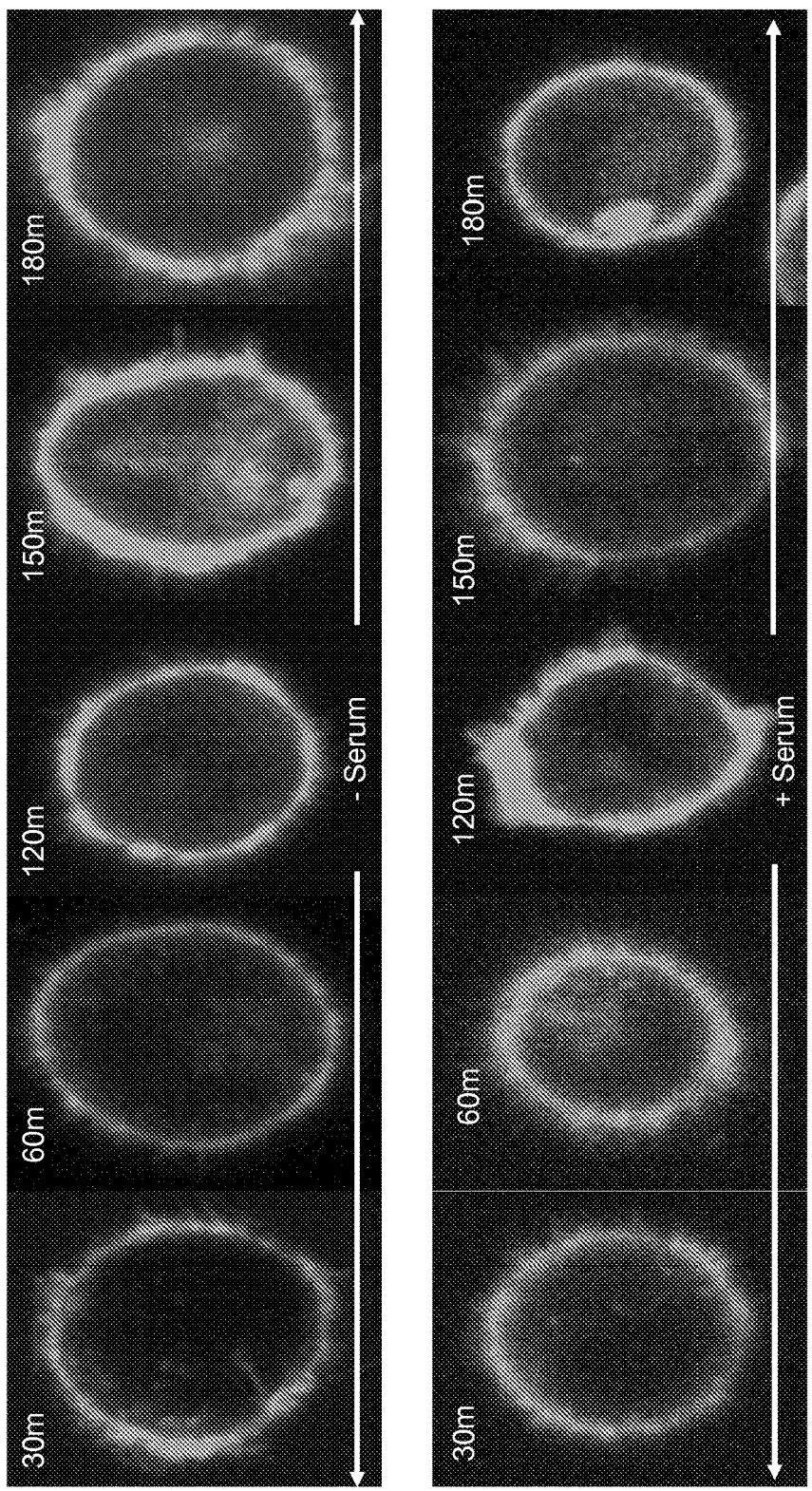
FIG. 9 is a series of confocal micrographs demonstrating the kinetic behavior of DMPE-PEG-FITC on the surface of MSCs at different time points (minutes) in the presence or absence of serum.

Kinetic Experiments:

MSCs labeled with DMPE-PEG (5 kDa)-FITC were incubated at 37° C. in the presence or the absence of 20% human serum for up to 3 hours. Residence of the DMPE-PEG-FITC on the surface of MSC was observed using FACS analysis and a confocal microscope. Regardless of serum, the fluorescence signal of the DMPE-PEG-FITC decreased gradually over time (Table 4), while no significant difference was found in confocal micrograph (see FIG. 9).

TABLE 4

Kinetics of the lipid-PEG on MSC surface.

| -Serum | | | +Serum | | |
| --- | --- | --- | --- | --- | --- |
| Min | % Gate | MFI | Min | % Gate | MFI |
| 10 | 100 | 121633 | 10 | 100 | 127255 |
| 30 | 100 | 114213 | 30 | 100 | 88379 |
| 60 | 100 | 91956 | 60 | 100 | 56928 |
| 90 | 100 | 82501 | 90 | 100 | 42627 |
| 120 | 100 | 82940 | 120 | 100 | 40208 |
| 150 | 100 | 77410 | 150 | 100 | 36158 |
| 180 | 100 | 76067 | 180 | 100 | 31545 |

Min: minutes;
% Gated: % of FITC+ MSC population;
MFI: mean fluorescence intensity No difference in MSC modification between culture expanded MSCs and freshly thawed MSCs were observed in any of the described experiments. MSCs thawed freshly from the stock were used in all subsequent experiments.

Figure 10:
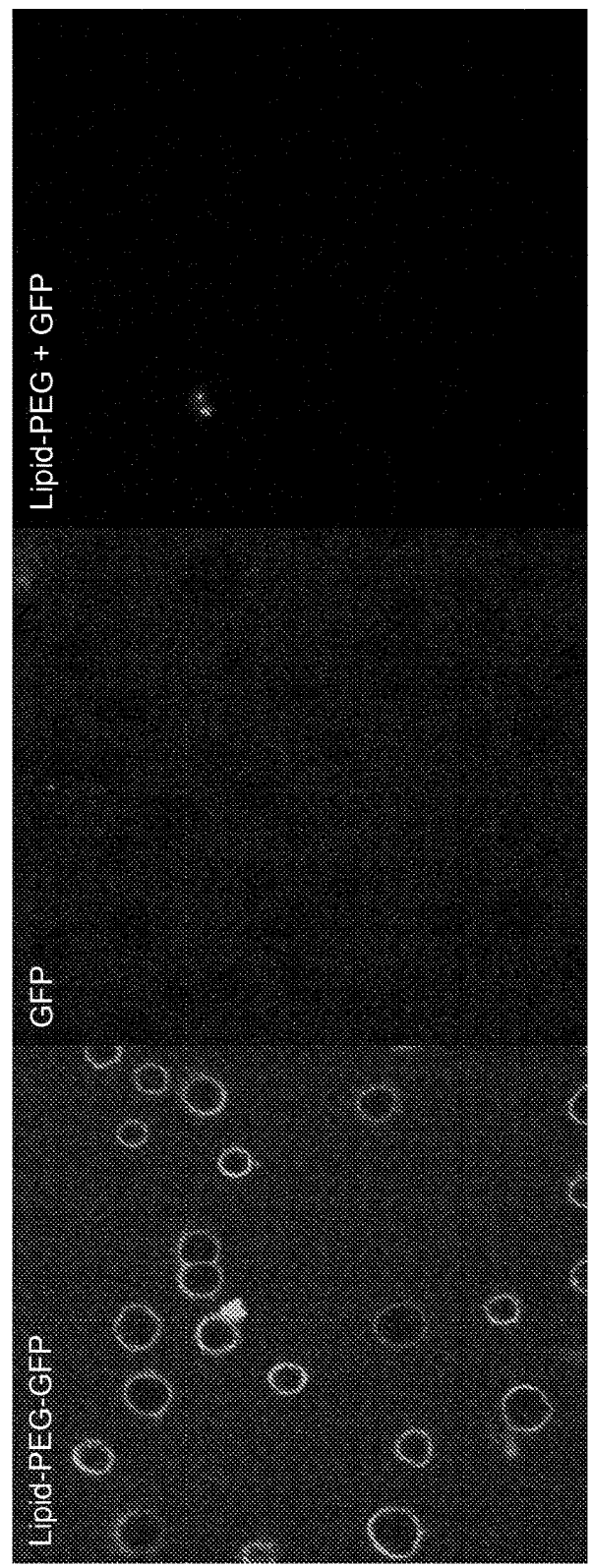
FIG. 10 is a series of confocal micrographs demonstrating MSCs modified with DMPE-PEG-GFP.

DMPE-PEG (5 kDa)-GFP Modified MSCs:

MSC stock was thawed and washed in complete culture media and suspended in plain culture media. The DMPE-PEG-GFP conjugate was incubated with MSCs for two minutes at room temperature. After the incubation, MSCs were harvested, washed, and suspended in HBSS Immobilization of GFP on the surface of MSCs was detected by confocal microscopy (see FIG. 10). GFP intensity was observed only on the surface of the MSCs treated with DMPE-PEG-GFP, while no GFP was detected in two control groups (GFP-only; GFP+DMPE-PEG).

Figure 11:
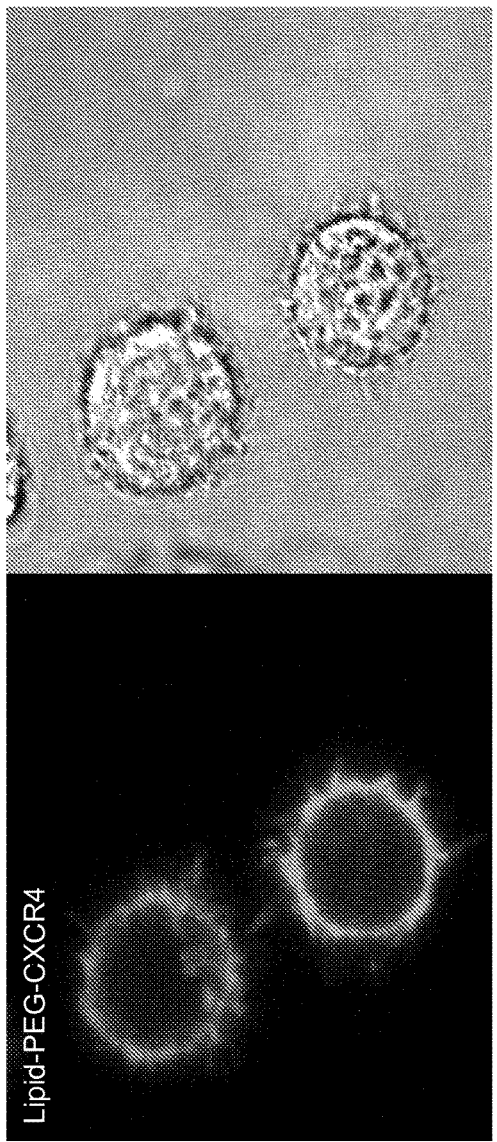
FIG. 11 is a confocal micrograph and FACS analysis graph of DMPE-PEG-CXCR4 modified MSCs.
Figure 11:
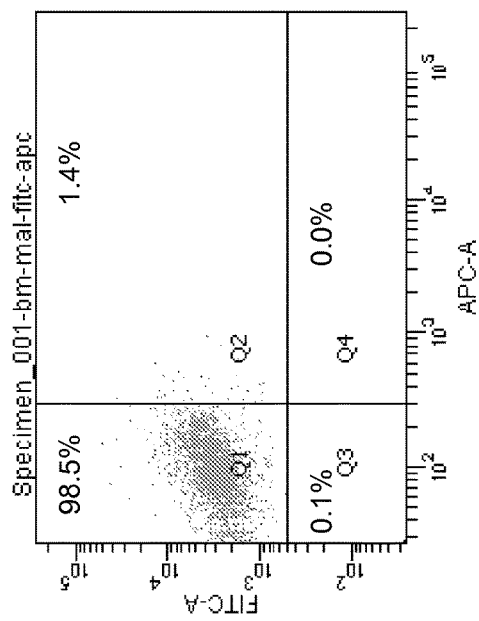

DMPE-PEG-CXCR4 Modified MSCs:

MSC stock was thawed and washed in complete culture media and suspended in plain culture media. FITC-labeled rCXCR4 was prepared and conjugated with DMPE-PEG to form a DMPE-PEG-rCXCR4 complex. The DMPE-PEG-rCXCR4 conjugate was incubated with MSCs for two minutes at room temperature. After the incubation, MSCs were harvested, washed, and suspended in HBSS. Confocal micrograph and FACS analysis demonstrated that greater than 98% of the MSCs contained rCXCR4 on their surface (see FIG. 11).

Example 3

SDF-1 Binding to rCXCR4 on the Surface of MSCs

Figure 12:
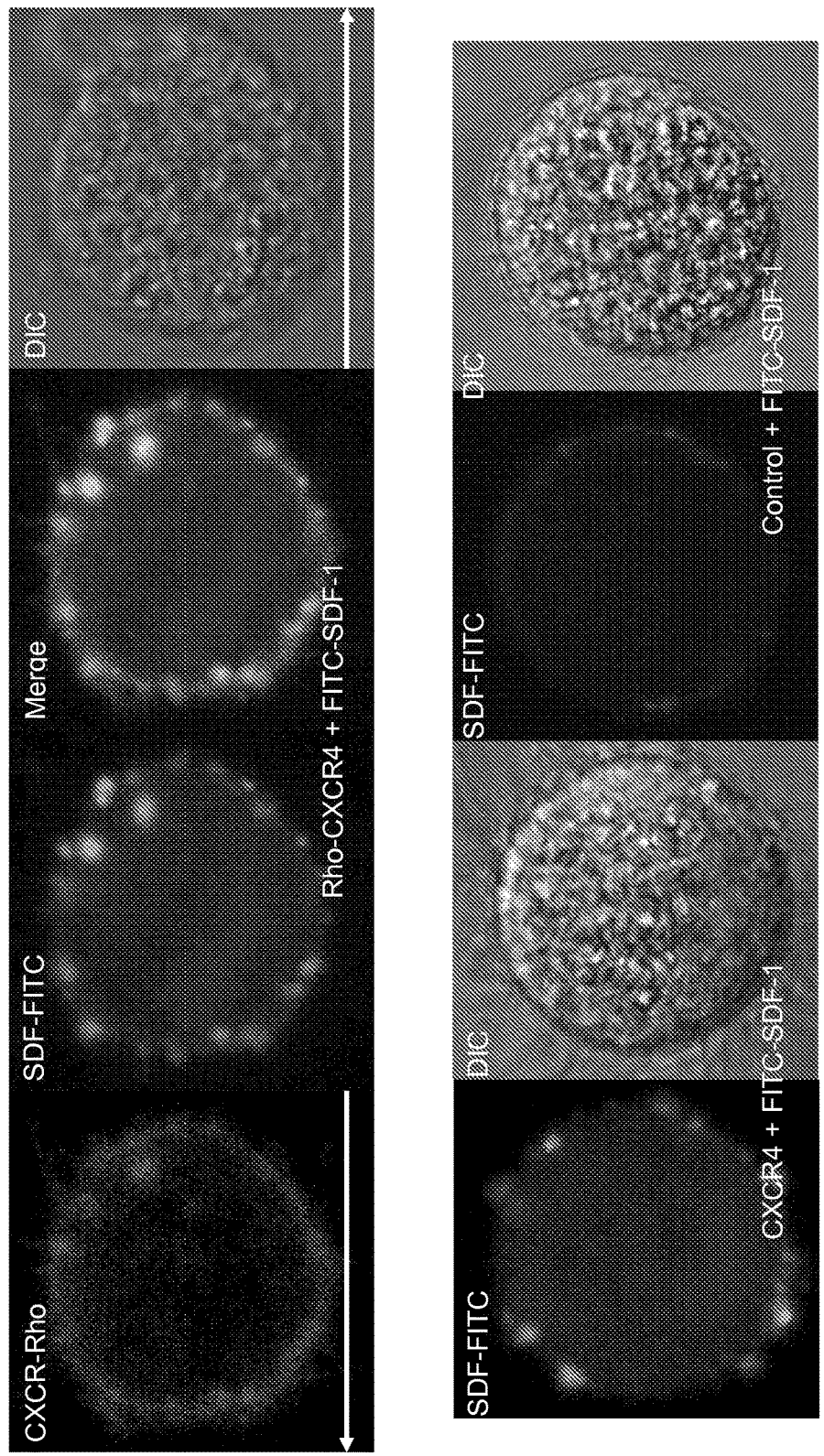
FIG. 12 is a series of confocal micrographs demonstrating SDF-1 binding with CXCR4 on the surface of an MSC.

FITC-labeled rSDF-1 (FITC-SDF-1) and rhodamine-labeled rCXCR4 (Rho-CXCR4) were prepared according to the manufacturer's protocol. MSCs were then modified with DMPE-PEG-Rho-CXCR4 or DMPE-PEG-CXCR4. Modified MSCs and non-modified MSCs were incubated with FITC-SDF-1 for 30 minutes of incubation at 4° C. under gentle shaking. Rho-CXCR4 was detected on the surface of the MSCs and FITC-SDF-1 was co-localized with CXCR4, confirming the binding of SDF-1 with CXCR4 on the surface of MSCs (see FIG. 12; Rho-CXCR4+FITC-SDF-1). In order to avoid unknown effects of rhodamine on the interaction between SDF-1 and CXCR4, FITC-SDF-1 was added to MSCs modified with DMPE-PEG-CXCR4. This group also showed SDF-1 binding on the surface of the MSCs (see FIG. 12; CXCR4+FITC-SDF-1), suggesting there was no artifact caused from rhodamine in co-localization. Weak SDF-1 intensity was detected on the surface of the non-modified MSCs (see FIG. 12; Control+FITC-SDF-1). This result indicates that CXCR4 disappeared during the culture expansion.

Figure 13:
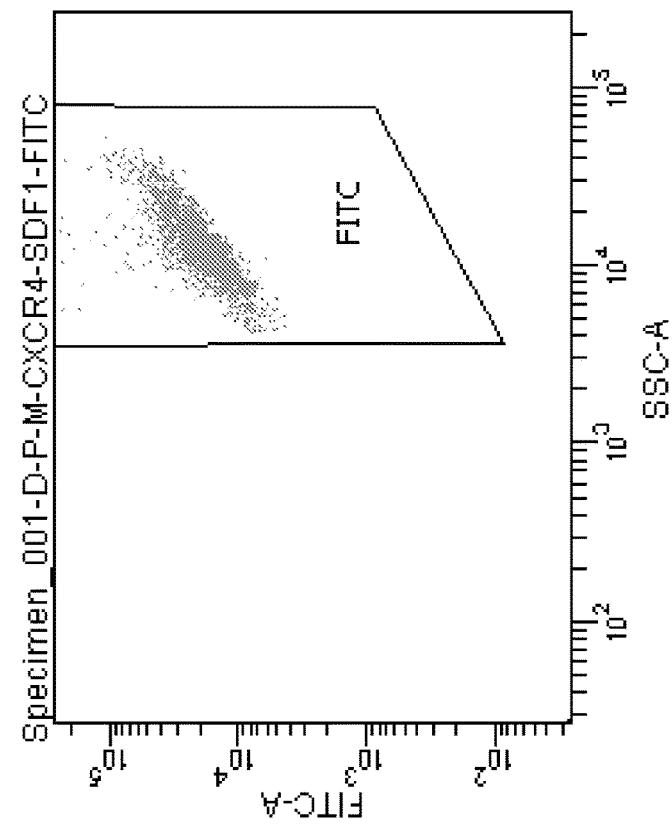
FIG. 13 is a confocal micrograph and a FACS analysis graph demonstrating SDF-1 binding with CXCR4 on the surface of an MSC.
Figure 13:
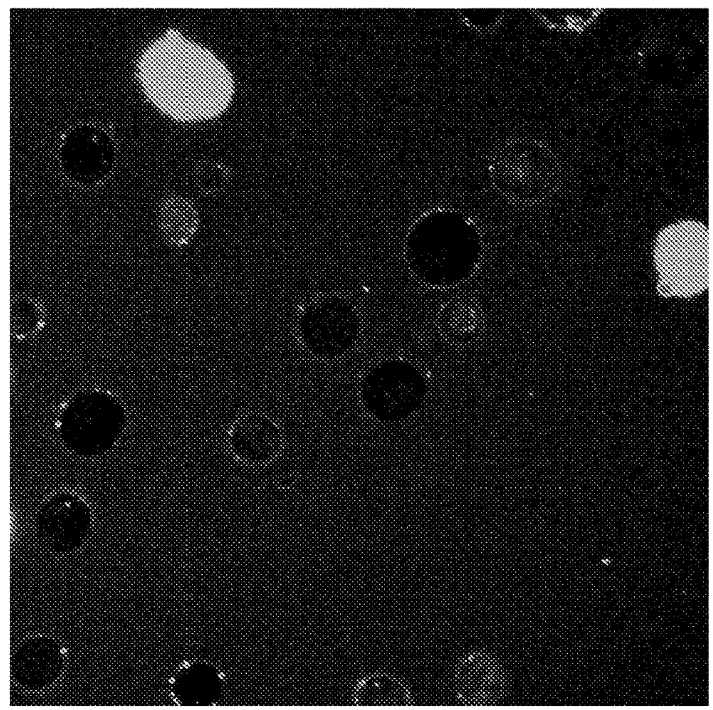

Additional evidence of SDF-1 binding to CXCR4 with CXCR4 detection on the surface of the MSC was achieved by the same methods as employed in the previous experiment. MSCs were modified with DMPE-PEG-CXCR4 and the modified MSCs were incubated with FITC-SDF-1. 100% of cells were FITC-positive and SDF-1 was observed only on the surface of MSCs (FIG. 13).

Taken together, these results confirm that MSCs modified by this technology are able to bind with SDF-1, providing a basis for MSC homing toward the SDF-1 gradient.

Example 4

MSC Migration Assay

CXCR4-MSCs were placed in the insert of a transwell system and the outer wells were filled with the culture media, with or without SDF-1. After 24 hours of incubation, use of an eye counting and cell counting kit determined migration of the CXCR4-MSCs toward the SDF-1 gradient. MSCs remaining on the topside of the insert were removed and MSCs on the bottom side of the insert were harvested and counted. To demonstrate dose dependency, varying amounts of DMPE-PEG-CXCR4 were added to fixed numbers of MSCs. MSCs with varying amounts of CXCR4 were plated in the transwell system as described above.

Figure 14:
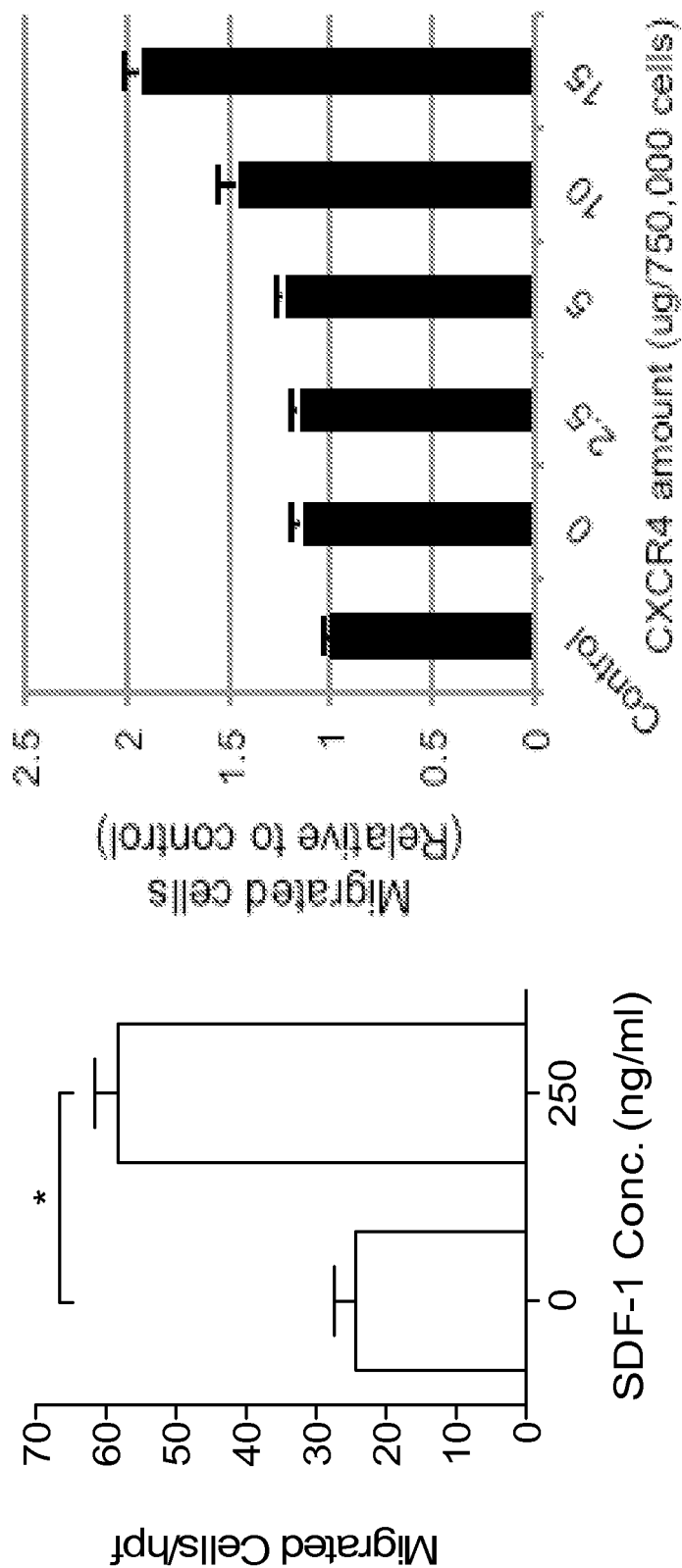
FIG. 14 is a series of graphs demonstrating DMPE-PEG-CXCR4 modified MSC migration toward SDF-1.

The number of MSCs that migrated in the presence of SDF-1 were >2-fold higher than the number of MSCs that migrated in the absence of SDF-1 (FIG. 14 left). Moreover, this experiment demonstrated that MSCs modified with varying doses of DMPE-PEG-CXCR4 migrated toward SDF-1 in a CXCR4 dose-dependent manner (FIG. 14 right).

Figure 15:
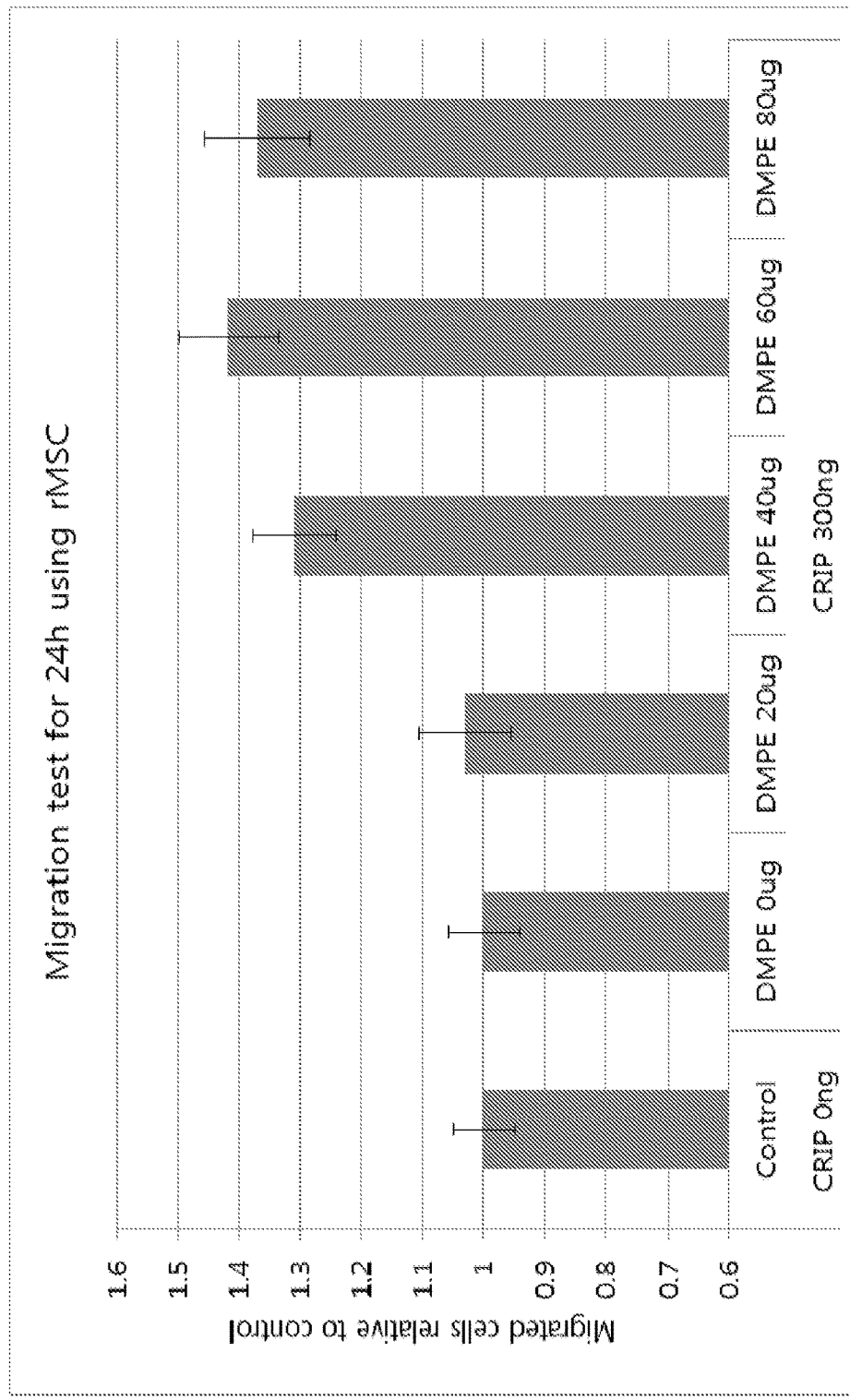
FIG. 15 is a graph demonstrating DMPE-PEG-CRPPR modified MSC migration toward CRIP2.

Using the same methods as described above for CXCR4-modified MSCs, CRPPR-modified MSCs demonstrated an ability to migrate toward CRIP2, the target ligand of the CRPPR peptide (see FIG. 15).

The invention claimed is:

1. A composition comprising the compound of formula (I)

L-Y-X-T       (I)

wherein
L is a phospholipid selected from the group consisting of 1,2-dimyristoyl-sn-glycero-3-phosphoethanolamine, 1,2-dipalmitoyl-sn-glycero-3-phosphoethanolamine and 1,2-distearoyl-sn-glycero-3-phosphocholine;
Y is a poly(ethylene glycol) having a molecular weight between about 2 kDa and about 10 kDa;
X is a linker derived from a reactive functional group; and
T is a targeting moiety adapted to bind to a target ligand.

2. The composition of claim 1, wherein L is 1,2-dimyristoyl-sn-glycero-3-phosphoethanolamine.

3. The composition of claim 1, wherein the poly(ethylene glycol) has a molecular weight of about 5 kDa.

4. The composition of claim 1, wherein the reactive functional group is selected from the group consisting of maleimide, N-hydroxysuccinimide, hydroxyl, amino, carboxyl, thiol, silane, and azide.

5. The composition of claim 1, wherein the target ligand is SDF-1.

6. The composition of claim 1, wherein the target ligand is CRIP2.

7. The composition of claim 1, wherein T is selected from the group consisting of a protein, a peptide, a glycoprotein, a glycopeptide, a steroid, a polysaccharide, a hormone, a cofactor, a nucleic acid, an antibody, a chimeric antigen receptor, and a drug.

8. The composition of claim 1, wherein T is a protein.

9. The composition of claim 8, wherein T is CXCR4.

10. The composition of claim 8, wherein T is CRPPR.

11. The composition of claim 9, wherein the reactive functional group is maleimide.

12. The composition of claim 1, further comprising a cell bound to the compound of formula (I), wherein L interacts hydrophobically with the lipid bilayer wall of the cell.

13. The composition of claim 12, wherein the cell is selected from the group consisting of a white blood cell, an endothelial cell, an hepatocyte, a kuppfer cell, an hepatic stellate cell, an allogeneic stem cell, a NK cell, a T cell, an endothelial progenitor cell, an hematopoietic stem cell, a pluripotent stem cell, an induced pluripotent stem cell, a lymphokine activated killer cell, a dendritic cell, and a mesenchymal stem cell.

14. The composition of claim 13, wherein the cell is a mesenchymal stem cell.

* * * * *